United States Patent
Lapidus et al.

(10) Patent No.: US 6,486,221 B2
(45) Date of Patent: Nov. 26, 2002

(54) ACTIVATION OF HYDROCARBON SYNTHESIS CATALYSTS WITH HYDROGEN AND AMMONIA

(75) Inventors: Albert L'Vovich Lapidus, Shosse (RU); Alla Jurievna Krylova, Ulitsa (RU)

(73) Assignee: ExxonMobil Research and Engineering Company, Annandale, NJ (US)

(*) Notice: Subject to any disclaimer, the term of this patent is extended or adjusted under 35 U.S.C. 154(b) by 0 days.

(21) Appl. No.: 09/865,796

(22) Filed: May 25, 2001

(65) Prior Publication Data

US 2001/0051663 A1 Dec. 13, 2001

Related U.S. Application Data

(62) Division of application No. 09/477,531, filed on Jan. 4, 2000, now Pat. No. 6,337,353.

(51) Int. Cl.$^7$ .............. C07C 27/00; B01J 23/00; B01J 23/24
(52) U.S. Cl. .............. 518/715; 502/325; 502/326
(58) Field of Search ............... 502/325, 326; 518/715

(56) References Cited

U.S. PATENT DOCUMENTS 4,659,742 A * 4/1987 Courty et al. ............... 518/713

FOREIGN PATENT DOCUMENTS

GB 728602 * 4/1955

* cited by examiner

*Primary Examiner*—Jafar Parsa
(74) *Attorney, Agent, or Firm*—Norby L. Foss

(57) ABSTRACT

A hydrocarbon synthesis catalyst is formed by contacting the catalyst precursor with a reducing gas comprising a mixture of hydrogen reducing gas and ammonia, at elevated temperature and pressure effective for conventional hydrocarbon synthesis catalyst formation by reduction in hydrogen.

8 Claims, No Drawings

ACTIVATION OF HYDROCARBON SYNTHESIS CATALYSTS WITH HYDROGEN AND AMMONIA

CROSS REFERENCE TO RELATED APPLICATION(S)

This application is a Divisional of U.S. Ser. No. 09/477,531 filed Jan. 4, 2000 now U.S. Pat. No. 6,337,353.

BACKGROUND OF THE DISCLOSURE

1. Field of the Invention

The invention relates to activating a hydrocarbon synthesis catalyst with hydrogen and ammonia. More particularly, the invention relates to forming an active hydrocarbon synthesis catalyst, including a Fischer-Tropsch type of hydrocarbon synthesis catalyst, by contacting a hydrocarbon synthesis catalyst precursor, comprising at least one catalytic metal component, with a reducing gas comprising a mixture of hydrogen and ammonia, at conditions effective to reduce the precursor and form an activated catalyst, and to a hydrocarbon synthesis process using the catalyst.

2. Background of the Disclosure

The synthesis of hydrocarbons, including oxygenated hydrocarbons such as methanol, from a synthesis gas comprising a mixture of $H_2$ and CO is well known. The synthesis gas feed is contacted with a Fischer-Tropsch catalyst at conditions effective for the $H_2$ and CO in the feed gas to react and form hydrocarbons. The synthesis is known as a Fischer-Tropsch hydrocarbon synthesis. Depending on the catalyst and conditions, the hydrocarbons may range from oxygenated compounds such as methanol and higher molecular weight alcohols, to high molecular weight paraffins which are waxy solids at room temperature. The process also makes, in lesser amounts, alkenes, aromatics, organic acids, ketones, aldehydes and esters. The synthesis is conducted in a fixed or fluidized catalyst bed reactor or in a liquid phase slurry reactor. Hydrocarbon synthesis catalysts are also well known and typically include a composite of at least one iron group catalytic metal component supported on, or composited with, with at least one inorganic refractory metal oxide support material, such as alumina, amorphous, silica-alumina, zeolites and the like. Various catalyst preparation methods have been used to form hydrocarbon synthesis catalysts, including impregnation, incipient wetness, compositing, ion exchange and other known techniques, to form a catalyst precursor. The precursor must be activated to form the catalyst. Typical activation methods include oxidation or calcination, followed by reduction in flowing hydrogen, multiple oxidation-reduction cycles and also reduction without prior oxidation. Examples of catalyst preparation and activation methods for Fischer-Tropsch hydrocarbon synthesis catalysts are disclosed in, for example, U.S. Pat. Nos. 4,086,262; 4,492,774 and 5,545,674.

SUMMARY OF THE INVENTION

The invention relates to forming an active hydrocarbon synthesis catalyst, including a Fischer-Tropsch type of hydrocarbon synthesis catalyst, by contacting a hydrocarbon synthesis catalyst precursor, comprising at least one catalytic metal component, with a reducing gas comprising a mixture of hydrogen and ammonia, at conditions of temperature and pressure effective to reduce the precursor and form an active catalyst, and to a hydrocarbon synthesis process using the activated catalyst. It has been found that forming the hydrocarbon synthesis catalyst by reducing the precursor, with a reducing gas comprising a mixture of hydrogen and ammonia, improves the properties of the resulting activated catalyst with respect to at least one of increased $C_{5+}$ selectivity, increased alpha (Schultz-Flory alpha) of the synthesis reaction and a reduction in methane make. These benefits are unexpected, in view of the fact that ammonia is a well known hydrocarbon synthesis catalyst poison. The catalyst precursor preferably comprises at least one catalytic metal component and at least one metal oxide catalyst support component.

The catalyst precursor may or may not be calcined prior to the reduction in the mixture of hydrogen and ammonia. The mixture of hydrogen and ammonia reducing gas may be substantialy comprised of hydrogen and ammonia or it may contain one or more diluent gasses which do not adversely effect or interfere with the activation, such as methane or argon and the like. The amount of ammonia present in the reducing gas will broadly range from 0.01 to 15 mole %, preferably 0.01 to 10 mole %, more preferably from 0.1 to 10 mole % and still more preferably from 0.5 to 7 mole %, based on the total gas composition. The hydrogen to ammonia mole ratio in the gas will range from 1000:1 to 5:1 and preferably from 200:1 to 10:1.

Thus, in one embodiment the invention is a process which comprises contacting a Fischer-Tropsch type of hydrocarbon synthesis catalyst precursor, comprising at least one catalytic metal component, and preferably at least one catalytic metal component and a metal oxide support type of component, with a reducing gas comprising a mixture of hydrogen and ammonia, at conditions effective to reduce the precursor and form an active catalyst. In another embodiment, the invention comprises a process for synthesizing hydrocarbons from a synthesis gas which comprises a mixture of $H_2$ and CO, wherein the synthesis gas contacts with a Fischer-Tropsch type of hydrocarbon synthesis catalyst, at reaction conditions effective for the $H_2$ and CO in the gas to react and form hydrocarbons and wherein the catalyst comprises a composite of at least one catalytic metal component and preferably also a metal oxide support component, and has been formed by contacting a catalyst precursor with a reducing gas comprising a mixture of hydrogen and ammonia, at conditions effective to reduce the precursor and form the catalyst. In a still further embodiment, at least a portion of the synthesized hydrocarbons are liquid at the synthesis reaction conditions. The conditions of temperature and pressure required to reduce the precursor and form a catalyst with a reducing gas comprising a mixture of hydrogen and ammonia in the practice of the invention, are the same conditions used for conventional hydrocarbon synthesis catalyst reduction and activation with hydrogen, in the absence of ammonia.

DETAILED DESCRIPTION

Hydrocarbon synthesis catalysts are well known and a typical Fischer-Tropsch hydrocarbon synthesis catalyst will comprise, for example, catalytically effective amounts of one or more Group VIII metal catalytic components such as Fe, Ni, Co and Ru. Preferably the catalyst comprises a supported catalyst, wherein the one or more support components of the catalyst will comprise an inorganic refractory metal oxide. The metal oxide support component is preferably one which is difficult to reduce, such an oxide of one or more metals of Groups III, IV, V, VI, and VII. The metal Groups referred to herein are those found in the Sargent-Welch Periodic Table of the Elements, © 1968. Typical support components include one or more of alumina, silica, and amorphous and crystalline aluminosilicates, such as zeolites. Particularly preferred support components are the Group IVB metal oxides, especially those having a surface area of 100 m²/g or less and even 70 m²/g or less. These support components may, in turn, be supported on one or more support materials. Titania, and particularly rutile titania, is a preferred support component, especially when the catalyst contains a cobalt catalytic component. Titania is a useful component, particularly when employing a slurry hydrocarbon synthesis process, in which higher molecular weight, primarily paraffinic liquid hydrocarbon products are desired. In some cases in which the catalyst comprises catalytically effective amounts of Co, it will also comprise one or more components or compounds of Re, Ru, Fe, Ni, Th, Zr, Hf, U, Mg and La, some of which are effective as promoters. A combination of Co and Ru is often preferred. Useful catalysts and their preparation are known and illustrative, but nonlimiting examples may be found, for example, in U.S. Pat. Nos. 4,568,663; 4,663,305; 4,542,122; 4,621,072 and 5,545,674.

The catalyst precursor is prepared by any convenient and known method, such as impregnation, incipient wetness, ion exchange, kneading, precipitation or coprecipitation, melt deposition or any other known compositing techniques. The catalytic metal component is typically applied as a solution of a compound of the metal that decomposes during the subsequent reduction or calcination, followed by reduction with the hydrogen and ammonia mixture according to the practice of the invention. For example, a cobalt component is typically applied to a support component as a nitrate salt. It is not uncommon to calcine the precursor after each application of reducible catalytic metal compound. After forming and extruding the precursor composite, it is typically pilled and dried. The precursor is then reduced or calcined and reduced, to form the catalyst. In the prior art, the reduction is achieved by contacting the precursor with flowing hydrogen or a hydrogen reducing gas, at conditions effective to reduce the catalytically active metal component (e.g., cobalt) to the metal form. A common method is known as the R-O-R method, in which the precursor is reduced in hydrogen, then calcined, followed by reducing again. In the prior art methods, the reducing hydrogen gas can be neat (all hydrogen), or mixed with one or more diluent gasses (e.g., methane, argon) which are inert towards the reduction. In the practice of the invention, the R-O-R method may also be used and a conventional hydrogen reducing gas employed for the first reduction, prior to calcination. However, in the practice of the invention, the second and final reduction, which is applied after the calcination, is achieved using a reducing gas comprising a mixture of hydrogen and ammonia. Typical reducing conditions effective for forming the catalyst comprising the reduced metal component on the support from the precursor, range from ½ to 24 hours, 200–500° C, 1–100 bar, and a GHSV of 50–10000. The actual conditions will depend on the hydrogen concentration in the reducing gas, as well as the metal to be reduced and its precursor form (e.g., salt or oxide). In the catalyst forming and activation process of the invention, the catalyst precursor which may or may not have been calcined, is contacted with a reducing gas comprising a mixture of hydrogen and ammonia, at typical reducing conditions, as set forth above, similar to those used for normal reduction. The precursor may be merely the dried composite without calcining, a calcined composite, or a composite in which multiple catalytic metal salt depositions have been made onto the support, with or without calcining after each deposition. In the case of the R-O-R procedure, the catalyst of the invention is formed if during the second, or final reduction, the reducing gas comprises the hydrogen and ammonia mixture. Catalyst activation may be conducted according to the process of the invention, either prior to loading it into the hydrocarbon synthesis reactor or in-situ in the hydrocarbon synthesis reactor.

The catalyst formed according to the process of the invention may be used in either a fixed bed, fluid bed or slurry hydrocarbon synthesis processes, for forming hydrocarbons from a synthesis gas comprising a mixture of $H_2$ and CO. These processes are well known and documented in the literature. In all of these processes, the synthesis gas is contacted with a suitable Fischer-Tropsch type of hydrocarbon synthesis catalyst, at reaction conditions effective for the $H_2$ and CO in the gas to react and form hydrocarbons. Depending on the process, the catalyst and synthesis reaction variables, some of these hydrocarbons will be liquid, some solid (e.g., wax) and some gas at standard room temperature conditions of temperature and pressure of 25° C. and one atmosphere, particularly if a catalyst having a catalytic cobalt component is used. In a fluidized bed hydrocarbon synthesis process, all of the products are vapor or gas at the reaction conditions. In fixed bed and slurry processes, the reaction products will comprise hydrocarbons which are both liquid and vapor at the reaction conditions. Slurry hydrocarbon synthesis processes are sometimes preferred, because of their superior heat (and mass) transfer characteristics for the strongly exothermic synthesis reaction and because they are able to produce relatively high molecular weight, paraffinic hydrocarbons when using a cobalt catalyst. In a slurry hydrocarbon synthesis process, a synthesis gas comprising a mixture of $H_2$ and CO is bubbled up as a third phase through a slurry in a reactor which comprises a particulate Fischer-Tropsch type hydrocarbon synthesis catalyst dispersed and suspended in a slurry liquid comprising hydrocarbon products of the synthesis reaction which are liquid at the reaction conditions. The mole ratio of the hydrogen to the carbon monoxide in the synthesis gas may broadly range from about 0.5 to 4, but is more typically within the range of from about 0.7 to 2.75 and preferably from about 0.7 to 2.5. The stoichiometric mole ratio for a Fischer-Tropsch hydrocarbon synthesis reaction is 2.0, but it can be increased to obtain the amount of hydrogen desired from the synthesis gas for other than the hydrocarbon synthesis reaction. In a slurry hydrocarbon synthesis process, the mole ratio of the $H_2$ to CO is typically about 2.1/1. Reaction conditions effective for the various hydrocarbon synthesis processes will vary somewhat, depending on the type of process, catalyst composition and desired products. Typical conditions effective to form hydrocarbons comprising mostly $C_{5+}$ paraffins, (e.g., $C_{5+}$–$C_{200}$) and preferably $C_{10+}$ paraffins, in a slurry process employing a catalyst comprising a supported cobalt component include, for example, temperatures, pressures and hourly gas space velocities in the range of from about 320–600° F., 80–600 psi and 100–40,000 V/hr/V, expressed as standard volumes of the gaseous CO and $H_2$ mixture (0° C., 1 atm) per hour per volume of catalyst, respectively. These conditions nominally apply to the other processes as well.

Hydrocarbons produced by a hydrocarbon synthesis process according to the practice of the invention are typically upgraded to more valuable products, by subjecting all or a portion of the $C_{5+}$ hydrocarbons to fractionation and/or conversion. By conversion is meant one or more operations in which the molecular structure of at least a portion of the hydrocarbon is changed and includes both noncatalytic processing (e.g., steam cracking), and catalytic processing (e.g., catalytic cracking) in which a fraction is contacted with a suitable catalyst. If hydrogen is present as a reactant, such process steps are typically referred to as hydroconversion and include, for example, hydroisomerization, hydrocracking, hydrodewaxing, hydrorefining and the more severe hydrorefining referred to as hydrotreating, all conducted at conditions well known in the literature for hydroconversion of hydrocarbon feeds, including hydrocarbon feeds rich in paraffins. Illustrative, but nonlimiting examples of more valuable products formed by conversion include one or more of a synthetic crude oil, liquid fuel, olefins, solvents, lubricating, industrial or medicinal oil, waxy hydrocarbons, nitrogen and oxygen containing compounds, and the like. Liquid fuel includes one or more of motor gasoline, diesel fuel, jet fuel, and kerosene, while lubricating oil includes, for example, automotive, jet, turbine and metal working oils. Industrial oil includes well drilling fluids, agricultural oils, heat transfer fluids and the like.

The invention will be further understood with reference to the examples below.

EXAMPLES

Example 1

Silica Support

A commercially available silica gel known as KCKG #4 (manufactured by Salavat Catalyst Factory of the Salavat Petrochemical Complex, Salavat, Russia), 2–4 mm diameter, was ground and sieved to obtain a 0.106–0.250 mm size fraction. This material was then calcined in flowing air at 450° C. for 5 hours, to form the support for the catalysts prepared below.

Example 2

Catalyst A Precursor

A solution of 5.18 gm of $Co(NO_3)_2 \cdot 6H_2O$ in 15 ml of distilled water was prepared. This solution was added to 21 ml (8.38 gm) of the calcined silica support from Example 1, with stirring, to form a catalyst precursor. Then the catalyst precursor was dried on a steam bath. At this stage, the catalyst precursor contained nominally 11 wt % cobalt and is the catalyst A precursor.

Example 3

Catalyst B Precursor

An aqueous solution of 4.9 gm of $ZrO(NO_3)_2 \cdot 2H_2O$ was added to 33.2 gm of the calcined silica support of Example 1, in a volume of water sufficient to fully wet the silica, which was then dried over a steam bath, followed by calcining in flowing air for 1 hour at 450° C., to form a first composite. Then a solution of 75 gm of $Co(NO_3)_2 \cdot 6H_2O$ in 30 ml of water was added to the composite which soaked for 2 hours at room temperature. The excess solution was decanted off and saved. The resulting second composite was dried on a steam bath and then calcined in flowing air for 2 hours at 450° C. After cooling, the saved excess solution was added to the second composite. The steps of soaking, decanting, drying, and calcining were repeated until all of the $Co(NO_3)_2 \cdot 6H_2O$ solution was impregnated onto the composite to form the final catalyst precursor, which is the catalyst B precursor. The so-formed catalyst B precursor contained 27 wt. % cobalt and 4.1 wt. % zirconium oxide.

Example 4

Catalyst B Reduction in $H_2$

The catalyst B precursor of Example 3 (20 ml) was mixed with 80 ml of 1–3 mm quartz particles and the mixture placed into a 25 mm ID quartz reactor. The catalyst/quartz mixture was held in place with glass wool at the bottom of the reactor and a layer consisting of 10 ml of the 1–3 mm quartz particles on top of the catalyst/quartz mixture. Hydrogen was then passed through the reactor at room temperature and atmospheric pressure at a gas hourly space velocity (GHSV) of 100 $hr^{-1}$ for 15 minutes. Prior to entering the reactor, the hydrogen was passed through a column of KOH pellets (pellet diameter nominally 3–5 mm) for removal of impurities. The reactor temperature was increased to 450° C. over 40–45 minutes. This condition was held for 5 hours. Then the reactor was allowed to cool to room temperature in flowing hydrogen. After the reactor had cooled, the hydrogen flow was replaced with a flow of 2:1 $H_2$:CO synthesis gas at 100 $hr^{-1}$ GHSV, for 15 minutes at atmospheric pressure. As with the hydrogen, the synthesis gas was passed through a column of KOH pellets for removal of impurities. Then valves were closed at the inlet and outlet of the reactor, storing the catalyst under the synthesis gas.

Example 5

Catalyst B Reduction in $NH_2$ and then $H_3/H_2$

A 20 ml sample of the catalyst B precursor of Example 3 was mixed with 80 ml of 1–3 mm quartz particles and the mixture placed into a 25 mm ID quartz reactor. The catalyst/quartz mixture was held in place with glass wool at the bottom of the reactor and a layer consisting of 10 ml of the 1–3 mm quartz particles on top of the catalyst/quartz mixture. Hydrogen was then passed through the reactor at room temperature and atmospheric pressure at a gas hourly space velocity (GHSV) of 100 $hr^{-1}$ for 15 minutes. Prior to entering the reactor, the hydrogen was passed through a column of KOH pellets (pellet diameter nominally 3–5 mm) for removal of impurities and through a 3-necked flask containing NaOH pellets. The center neck of the 3-necked flask was equipped with a syringe for addition of 29 wt % $NH_3/71$ wt % $H_2O$ solution. The NaOH in the 3-necked flask served to absorb the water from the $NH_3/H_2O$ solution, liberating the $NH_3$ vapor, which was then swept out of the flask and into the reactor. The reactor temperature was increased to 400° C. over 40–45 minutes. In preparing the catalysts, the procedure used in Example 4 (in which the reactor temperature was increased from room temperature to 450° C. over 40–45 minutes and held at 450° C. for 5 hours) was used until the reactor reached the 450° C. temperature. This was followed by 5 hours of reduction (i) with $H_2$ only for the first sample, (ii) with $H_2$ followed a mixture of $H_2$ and $NH_3$ for the next four samples and (iii) with a mixture of $H_2$ and $NH_3$ only for the fifth sample, as shown in Table 2 below. Ammonia addition into the $H_2$ gas to provide the $H_2/NH_3$ reducing gas mixture, was achieved by a continuous drop-wise addition of the 29 wt % $NH_3/71$ wt % $H_2O$ solution from the syringe. The nominal concentration of $NH_3$ in the reducing gas during the $NH_3/H_2O$ solution addition was 5 mole %. Irrespective of whether the reduction was achieved with (i) all $H_2$, (ii) $H_2$ followed by the $H_2/NH_3$, or (iii) all $H_2/NH_3$, the total reduction time was 5 hours, as shown in Table 2. Following reduction, the reactor was allowed to cool to room temperature in flowing hydrogen. After the reactor had cooled, the hydrogen flow was replaced with a flow of 2:1 $H_2$:CO synthesis gas at 100 $hr^{-1}$ GHSV for 15 minutes at atmospheric pressure. As with the hydrogen, the synthesis gas was passed through a column of KOH pellets, for removal of impurities. Then valves were closed at the inlet and outlet of the reactor, storing the catalyst under the synthesis gas.

Example 6

Catalyst A Reduction with $NH_3/H_2$

A 20 ml sample of the catalyst A precursor of Example 2 was mixed with 80 ml of 1–3 mm quartz particles and the mixture placed into a 25 mm ID quartz reactor. The catalyst/quartz mixture was held in place with glass wool at the bottom of the reactor and a layer consisting of 10 ml of the 1–3 mm quartz particles on top of the catalyst/quartz mixture. Hydrogen was then passed through the reactor at room temperature and atmospheric pressure at a gas hourly space velocity (GHSV) of 3000 $hr^{-1}$ for 15 minutes. Prior to entering the reactor, the hydrogen was passed through a column of KOH pellets (pellet diameter nominally 3–5 mm) for removal of impurities and through a 3-necked flask containing NaOH pellets. The center neck of the 3-necked flask was equipped with a syringe for addition of 29 wt % $NH_3$/71 wt % $H_2O$ solution. The NaOH in the 3-necked flask served to absorb the water from the $NH_3/H_2O$ solution, liberating the $NH_3$ vapor, which was then swept out of the flask to the reactor. The reactor temperature was increased to 400° C. over 40–45 minutes. After reaching 400° C., dropwise addition of the 29 wt % $NH_3$/71 wt % $H_2O$ solution was commenced from the syringe. The addition rate was varied to give a nominal concentration of $NH_3$ in the reducing gas between 0 ($H_2$-only) and 3.0 mole %. This condition was held for 1 hour. Then the reactor was allowed to cool to room temperature in flowing hydrogen. After the reactor had cooled, the hydrogen flow was replaced with a flow of 2:1 $H_2$:CO synthesis gas at 100 $hr^{-1}$ GHSV, for 15 minutes at atmospheric pressure. As with the hydrogen, the synthesis gas was passed through a column of KOH pellets for removal of impurities. Then valves were closed at the inlet and outlet of the reactor, storing the catalyst under the synthesis gas.

Example 7

Testing of Catalyst A

The flow of synthesis gas into the reactor was resumed with the catalyst of Example 6 (Catalyst A reduced with $H_2+NH_3$) at 100 $hr^{-1}$ GHSV and 1 atm pressure. Prior to entering the reactor, the synthesis gas was passed through a column of KOH pellets (pellet diameter nominally 3–5 mm) for removal of impurities. The synthesis gas composition was 2:1 $H_2$:CO by volume. The reactor temperature was increased from room temperature to 160° C. in about 40 minutes. This condition was held for 5 hours, after which the reactor was cooled down to room temperature in the flowing synthesis gas and the catalyst stored under the synthesis gas as described in Example 6. Testing was resumed the next day following the same procedure, except that the test temperature was 10° C. higher. This was repeated each day until the optimum operating temperature was found. The optimum operating temperature was defined as the temperature where the yield of $C_{5+}$ products is maximized, as measured in gm of $C_{5+}$ product per standard cubic meter of synthesis gas fed to the reactor. Finding the optimum operating temperature entailed increasing the reactor temperature in 10° C. steps until the $C_{5+}$ yield decreased from the previous test. The temperature from the previous test is the optimum temperature. Catalyst performance was determined by measuring the gas contraction, product gas composition by gas chromatography, and $C_{5+}$ liquid product yield. The $C_{5+}$ liquid product was recovered form the reactor effluent using two traps. The first trap was water cooled and the second was cooled with dry ice/acetone (−80° C.). The $C_{5+}$ product in the first trap was weighted directly. The liquid product in the second trap was first warmed to room temperature, to vaporize $C_{4-}$ components prior to weighing. The combined weights of the hydrocarbon liquid product in both traps was used to determine the $C_{5+}$ product yield. The $C_{5+}$ product from the optimum temperature was further analyzed, to determine hydrocarbon type and carbon chain length distribution. From time to time, the $C_{5+}$ products from the non-optimum temperature tests were combined and analyzed. The catalyst precursor was not calcined prior to reduction in these experiments. The results are shown in Table 1 below.

TABLE 1

| Mole % $NH_3$ in Reducing Gas | Optimum Temp., ° C. | CO Conversion % | Yield, gm/m³ of Gas Feed | | Selectivity, % | | Alpha |
|---|---|---|---|---|---|---|---|
| | | | $CH_4$ | $C_{5+}$ | $C_{4-}$ | $C_{5+}$ | |
| 0 | 200 | 60 | 26 | 78 | 40 | 60 | 0.8 |
| 0.5 | 210 | 45 | 9 | 76 | 37 | 76 | 0.84 |
| 0.75 | 210 | 49 | 24 | 70 | 43 | 57 | 0.85 |
| 1 | 210 | 58 | 21 | 72 | 42 | 58 | 0.84 |
| 2 | 200 | 42 | 10 | 72 | 20 | 80 | 0.84 |
| 3 | 210 | 24 | 4 | 40 | 25 | 75 | 0.85 |

These results demonstrate the effect on catalyst performance, of the $NH_3$ concentration in the reducing gas used to convert the precursor to the catalyst. Up to about 2 mole % $NH_3$ in the reducing gas, both the % CO conversion and $C_{5+}$ yields are good, with the $C_{5+}$ selectivity peaking at about 80%. Although the catalyst activity decreased when $NH_3$ was used in the reducing gas, the reduction is mainly from the $C_{4-}$ gas products. The Schultz-Flory alpha also increased when the catalyst reducing gas contained $NH_3$ and stayed essentially constant from 0.5 to 3.0 mole % $NH_3$ in the reducing gas. These results show that the presence of $NH_3$ in the reducing gas during catalyst reduction, improved catalyst performance. Thus, in all cases, reduction in the presence of $NH_3$ increased the alpha of the hydrocarbon synthesis reaction. The greatest difference between having and not having $NH_3$ in the reducing gas, is seen for the run in which the $H_2$ reducing gas contained 0.5 mole % $NH_3$. This produced a $C_{5+}$ selectivity of 76%, with a high yield of $C_{5+}$ hydrocarbons and only a 9% methane make. At 2 mole % $NH_3$, the $C_{5+}$ selectivity was even higher and the $C_{5+}$ yield, while lower, was still good.

Example 8

Catalyst B Testing after Reduction with $H_2$ and then with $H_2+NH_3$)

The synthesis gas flow was resumed into the reactor with the catalyst of Example 5 (Catalyst B reduced first with $H_2$ then with $H_2+NH_3$) at 100 $hr^{-1}$ GHSV and 1 atm pressure. Prior to entering the reactor, the synthesis gas was passed through a column of KOH pellets (pellet diameter nominally 3–5 mm) for removal of impurities. The synthesis gas composition was 2:1 $H_2$:CO by volume. The reactor temperature was increased from room temperature to 160° C. in about 40 minutes. This condition was held for 5 hours, after which the reactor was cooled to room temperature in the flowing synthesis gas and the catalyst stored under the synthesis gas. Testing was resumed the next day following the same procedure, except that the test temperature was 10° C. higher. This was repeated each day until the operating temperature was 190° C. At 190° C. the catalyst performance was determined by measuring the gas contraction, product gas composition by gas chromatography, and $C_{5+}$ liquid product yield. The $C_{5+}$ liquid was recovered form the reactor effluent using two traps. The first trap was water cooled and the second was cooled with dry ice/acetone (−80° C.). The $C_{5+}$ product in the first trap was weighted directly. The liquid product in the second trap was first warmed to room temperature to vaporize $C_{4-}$ components prior to weighing. The combined weights of the hydrocarbon liquid product in both traps was used to determine the $C_{5+}$ product yield. The $C_{5+}$ product from the optimum temperature was further analyzed to determine hydrocarbon type and carbon chain length distribution. From time to time, the $C_{5+}$ products from the non-optimum temperature tests were combined and analyzed. The catalyst precursor used in these experiments was calcined prior to reduction. It should be noted that while the cobalt oxide formed by the calcination converts to the metal during the reduction, the zirconium component remains as the oxide and is not reduced to the metal. The results at 190° C. are shown in Table 2 below

TABLE 2

| Reduction Time, Hours* | | CO Conversion | Yield, gm/m³ of Gas Feed | | Selectivity, % | | |
|---|---|---|---|---|---|---|---|
| $H_2$ | $H_2 + NH_3$ | % | $CH_4$ | $C_{5+}$ | $C_{4-}$ | $C_{5+}$ | Alpha |
| 5 | 0 | 87 | 34 | 87 | 53 | 47 | 0.75 |
| 4 | 1 | 72 | 10 | 90 | 23 | 77 | 0.76 |
| 3 | 2 | 58 | 8 | 97 | 19 | 81 | 0.82 |
| 2 | 3 | 50 | 8 | 96 | 16 | 84 | 0.86 |
| 1 | 4 | 46 | 9 | 84 | 20 | 80 | 0.82 |
| 0 | 5 | 47 | 11 | 70 | 24 | 76 | 0.81 |

*Total reduction time of 5 hours in each case. Number in $H_2$ column is reducing time under hydrogen, before switching to a mixture of $H_2$ and $NH_3$ (5 mole %).

Table 2 shows how, at a constant reducing time of 5 hours, the performance of Catalyst B is affected by the presence of $NH_3$ in the $H_2$ reducing gas, when sequentially reduced with $H_2$ followed by $H_2+NH_3$, and also when reduced in only $H_2+NH_3$. It should be noted, that tests revealed optimum catalytic properties for the catalyst reduced under hydrogen, at a hydrogen treat gas ratio of 100 hr $^{-1}$ GHSV, were achieved at a reduction time of five hours. This is why the total reduction time of 5 hours was chosen for this experiment. However, a portion of the metal reduction and concomitant activation is achieved in one hour. Thus, an active catalyst existed prior to contact with the hydrogen and ammonia reducing gas, for the runs in Table 2 above, in which the contact time with the hydrogen reducing gas was, 1, 2, 3 and 4 hours. In the last run in the Table, it was a precursor that was contacted with the hydrogen and ammonia mixture for 5 hours. Thus, these four runs and the first run with only hydrogen reduction are presented for comparative purposes. However, the last run the precursor was completely reduced to form a catalyst with a reducing gas comprising a mixture of hydrogen and ammonia. The data show that this catalyst, produced by the process of the invention, had less methane make, greater $C_{5+}$ selectivity and a higher alpha than the prior art catalyst of the first run, in which complete reduction and catalyst formation was achieved using only hydrogen for the reduction.

As Table 2 shows, in the second through the fifth runs, the precursor was at least partially reduced prior to contact with the hydrogen and ammonia mixture. With 4 hours on $H_2$, followed by only 1 hour on $H_2+NH_3$, a sharp increase in the $C_{5+}$ yield and selectivity occurred, with a concomitantly sharp drop in methane make. Thus, Increasing the reduction time with $H_2+NH_3$ caused the $C_{5+}$ yield, $C_{5+}$ selectivity, and Schulz-Flory alpha to peak, between 2 to 4 hours of $H_2+NH_3$ reduction. Although the catalyst activity drops with increasing $H_2+NH_3$ reduction time, the activity drop is taken from the $C_{4-}$ gas, leaving the yield of $C_{5+}$ approximately constant up to three hours of the $H_2/NH_3$ treatment. More than three hours decreased the $C_{5+}$ yield and selectivity, but the alpha of the reaction remained high. This shows that introduction of $NH_3$ into the reducing gas, during at least a portion of the catalyst reduction, is effective in improving catalyst performance.

It is understood that various other embodiments and modifications in the practice of the invention will be apparent to, and can be readily made by, those skilled in the art without departing from the scope and spirit of the invention described above. Accordingly, it is not intended that the scope of the claims appended hereto be limited to the exact description set forth above, but rather that the claims be construed as encompassing all of the features of patentable novelty which reside in the present invention, including all the features and embodiments which would be treated as equivalents thereof by those skilled in the art to which the invention pertains.

What is claimed is:

1. A process for forming a Fisher-Tropsch catalyst comprising contacting a hydrocarbon synthesis catalyst precursor, consisting essentially of at least one Group VIII metal component or mixtures thereof, on a catalyst support, with a reducing gas comprising a mixture of hydrogen and ammonia, at conditions effective to reduce said precursor and form said catalyst.

2. A process according to claim 1 wherein said catalyst support comprises a metal oxide catalyst support component.

3. A process according to claim 1 wherein said ammonia is present in said reducing gas in an amount of from 0.01 to 15 mole % of the total reducing gas composition.

4. A process according to claim 3 wherein the hydrogen to ammonia mole ratio in said reducing gas ranges from 1000:1 to 5:1.

5. A process according to claim 4 wherein said catalytic metal component comprises at least one of Co and Ru.

6. A process according to claim 5 wherein said support component includes at least one component selected from the group consisting of alumina, silica, alumino-silicates and titania.

7. A process according to claim 6 wherein said ammonia is present in said reducing gas in an amount of from 0.1 to 10 mole % of the total reducing gas composition and wherein said hydrogen to ammonia mole ratio in said reducing gas ranges from 200:1 to 10:1.

8. A catalyst made according to the process of claim 1.

* * * * *